United States Patent [19]
Kitajima et al.

[11] Patent Number: 5,270,747
[45] Date of Patent: Dec. 14, 1993

[54] STEREOMICROSCOPE WITH FIRST AND SECOND ILLUMINATING SYSTEMS

[75] Inventors: Nobuaki Kitajima; Kazutoshi Takagi, both of Tokyo, Japan

[73] Assignee: Kabushiki Kaisha Topcon, Tokyo, Japan

[21] Appl. No.: 973,550

[22] Filed: Nov. 9, 1992

Related U.S. Application Data

[63] Continuation of Ser. No. 626,112, Dec. 14, 1990, abandoned.

[30] Foreign Application Priority Data

Dec. 14, 1989 [JP] Japan .................. 1-325657

[51] Int. Cl.$^5$ ............................ A61B 3/10
[52] U.S. Cl. .................. 351/205; 351/214; 351/221
[58] Field of Search ............ 351/205, 206, 207, 208, 351/214, 221; 359/387, 389, 375, 376, 377

[56] References Cited

U.S. PATENT DOCUMENTS

| | | | |
|---|---|---|---|
| 3,512,860 | 5/1970 | Hansen et al. | 359/389 |
| 3,664,730 | 5/1972 | Cardona | 351/205 X |
| 4,710,000 | 12/1987 | Spitnaz et al. | 351/205 X |
| 4,830,483 | 5/1989 | Kohayakawa et al. | 351/205 X |

Primary Examiner—Rodney B. Bovernick
Assistant Examiner—Hung Xuan Dang
Attorney, Agent, or Firm—Finnegan, Henderson, Farabow, Garrett & Dunner

[57] ABSTRACT

A stereomicroscope has an objective lens facing an eye, and the first and the second observing optical systems for three-dimensionally observing the eye through the objective lens. The stereomicroscope also has the first and the second illuminating systems for illuminating the eye around the optical axes of the first and second observing optical systems.

4 Claims, 10 Drawing Sheets

STEREOMICROSCOPE WITH FIRST AND SECOND ILLUMINATING SYSTEMS

This application is a continuation of application Ser. No. 07/626,112, filed Dec. 14, 1990, now abandoned.

BACKGROUND OF THE INVENTION

1. Field of the Invention

This invention relates to a stereomicroscope including an objective lens disposed opposite to an eye, and the first and the second observing optical systems for three-dimensionally observing the eye.

2. Prior Art of the Invention

Heretofore, a stereomicroscope used for a surgical operation, for example, an operation for cataracta and the like has been known.

Figure 9:
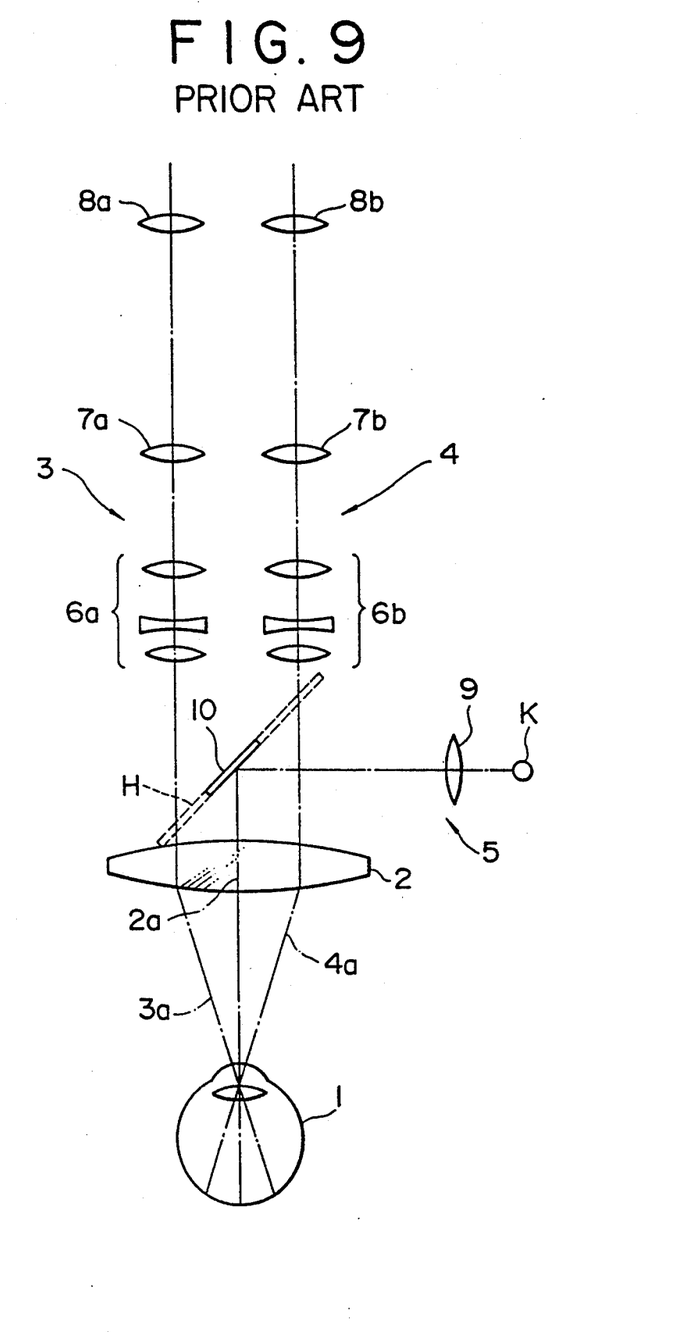
FIG. 9 is an explanatory view showing the arrangement of the optical system of the conventional stereomicroscope.

The stereomicroscope of this type, as shown in FIG. 9, includes an objective lens 2 disposed opposite to an eye 1, the first and the second observing optical systems 3 and 4 for three-dimensionally observing the eye 1 through the objective lens 2, and an illuminating optical system 5 for illuminating the eye 1.

The first and second observing optical systems 3 and 4 comprises zoom lenses 6a and 6b, imaging lenses 7a and 7b, and oculars 8a and 8b, while the illuminating optical system 5 comprises an illuminating light source K, a condenser lens 9, and a mirror 10.

When the eye 1 is illuminated by the illuminating optical system 5, the eye 1 can be three-dimensionally observed at a predetermined magnification by operating the zoom lenses 6a and 6b.

By the way, an operation for cataract is performed in such a manner as to cut out the fore-brain of a crystal body and to take out turbidity. However, when the rest amount of turbidity becomes little, the turbidity is illuminated utilizing a reflected light on the eye fundus. The reason is that if a little amount turbidity is directly illuminated by the illuminating optical system 5, it becomes difficult to observe the turbidity.

Figure 10:
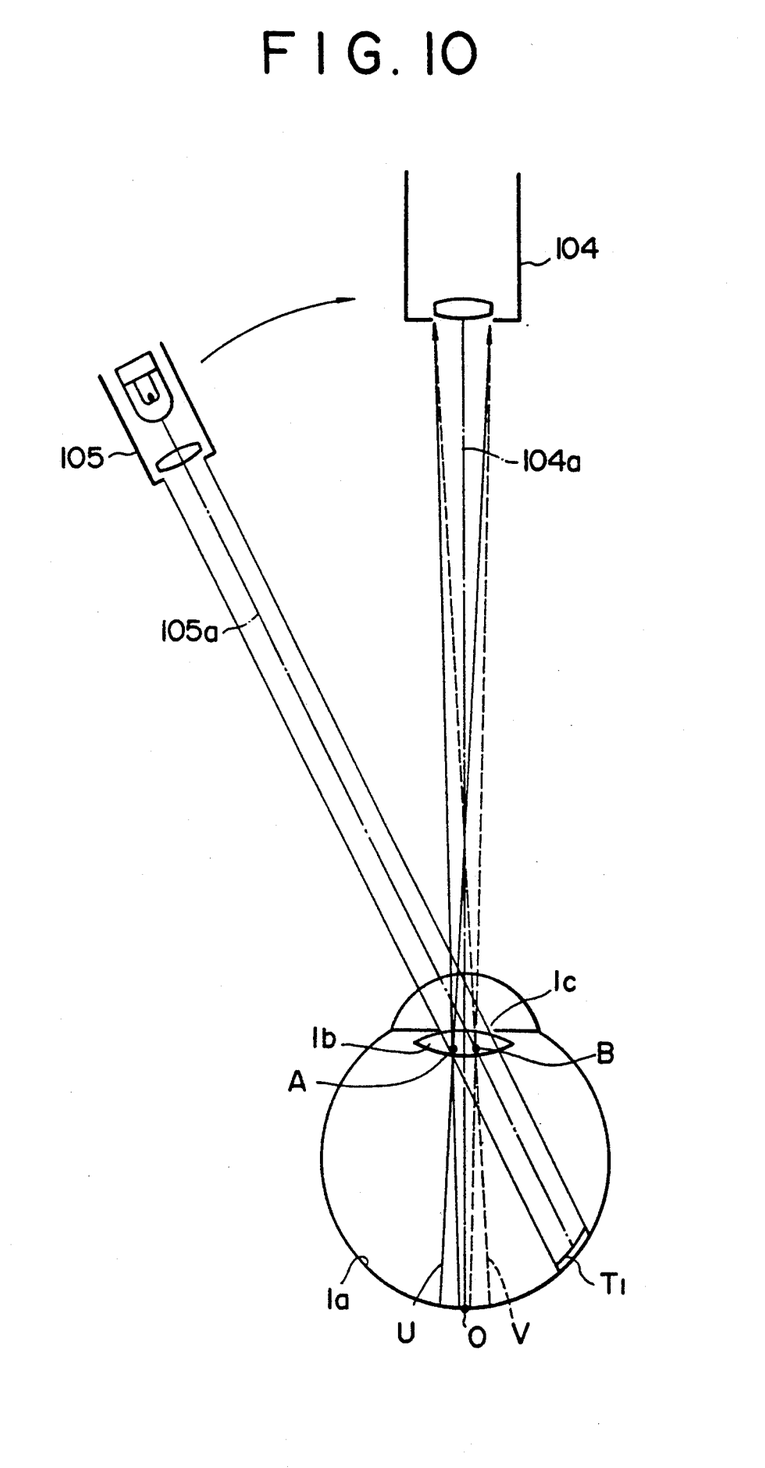
FIG. 10 is an explanatory view showing the relation between the illuminating optical system for explaining the brightness of the pupil area and the observing optical system.
Figure 11:
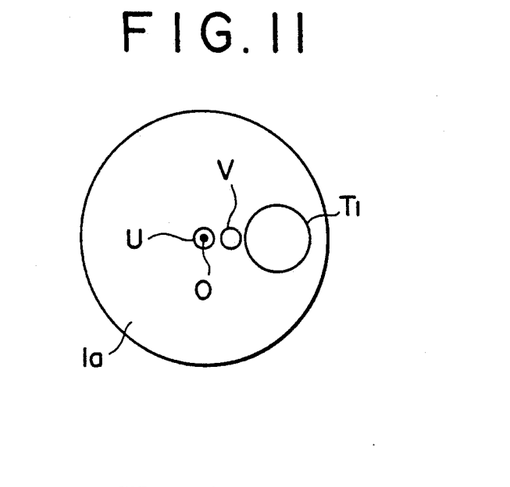
FIGS. 11, 13 and 15 are explanatory views showing the illuminated area of the eye fundus.
Figure 12:
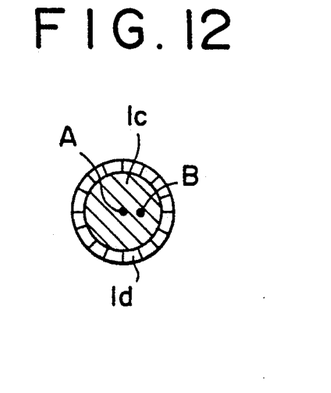
FIGS. 12, 14 and 16 are explanatory views of the pupil areas when looked from the observing optical system.

However, when the optical axis 105a of the illuminating optical system 105 is different from the optical axis 104a of the observing optical system 104 as shown in FIG. 10 an illuminated area T1 by the illuminating optical system 105 on the eye fundus 1a is displaced from the spot O on the optical axis of the observing optical system 104 as shown in FIG. 11. And a reflected pencil of rays by the illuminated area T1 proceeds toward the illuminating optical system 105. As a result, when the crystal body 1b is observed from the observing optical system 104, the reflected light from the eye fundus 1a scarcely enters to the observing optical system 104, and a pupil area 1c is observed dark as shown in FIG. 12.

Therefore, when the crystal body 1b includes, for example, turbidities A and B, the turbidities A and B are not illuminated by reflected light from the eye fundus and observation of the turbidities A and B becomes difficult. In FIG. 11, the characters U, V, denote pencils of rays to be converged to the turbidities A and B by reflection from the eye fundus 1a. The symbolic character 1d in FIG. 12 denotes an iris.

Figure 13:
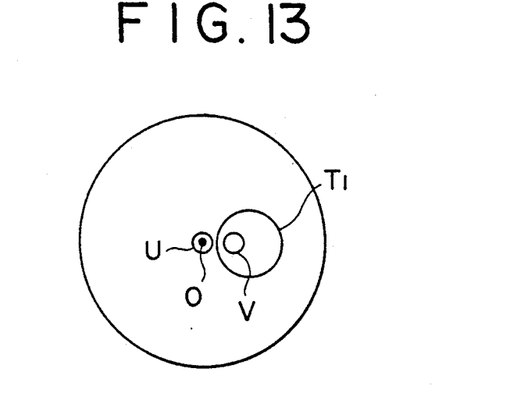
Figure 14:
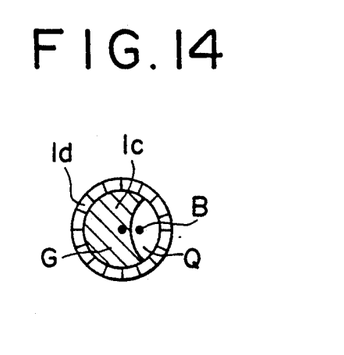

When the illuminating optical system 105 is approached to the observing optical system 104 and the illuminated area T1 of the illuminating light reaches the spot O including a pencil of rays V as shown in FIG. 13, the peripheral pencil of rays including V among the reflected light by the illuminated area T1 in FIG. 13 enters the observing optical system 104. Owing to the foregoing, the pupil area 1c looked from the observing optical system 104, as shown in FIG. 14 is dark at an area G including the turbidity A and bright at an area Q including the turbidity B.

Figure 15:
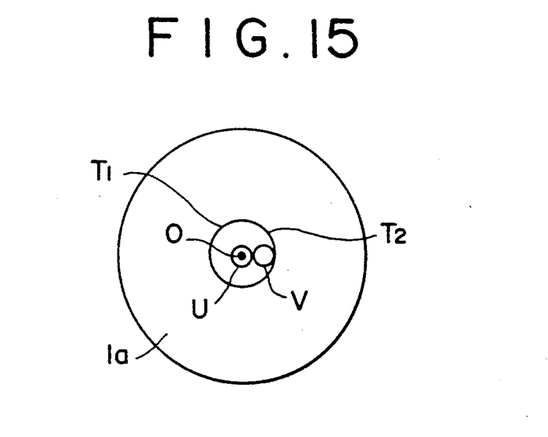
Figure 16:
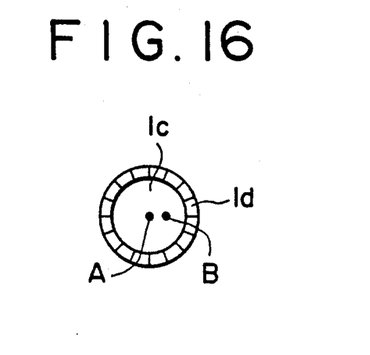
Figure 17:
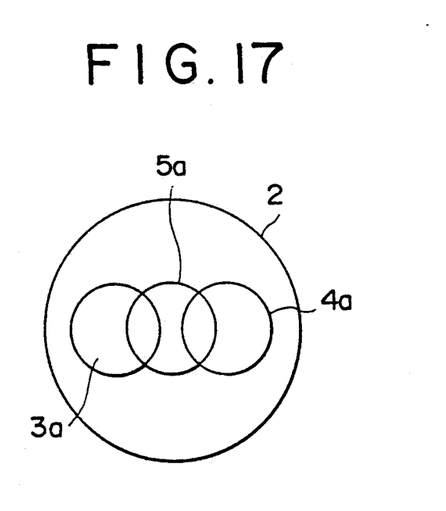
FIG. 17 is an explanatory view showing an illuminating optical path and an observing optical path on the objective lens.

When the optical axis 105a of the illuminating optical system 105 and the optical axis 104a of the observing optical system 104 are aligned, the wost of the reflected pencil of rays by the illuminating area T1 shown in FIG. 15 enters the observing optical system 15. As a result, the pupil area 1c, when looked from the observing optical system 104, it comes to have a uniform brightness owing to the reflected light from the illuminated area T1 as shown in FIG. 16.

Figure 18:
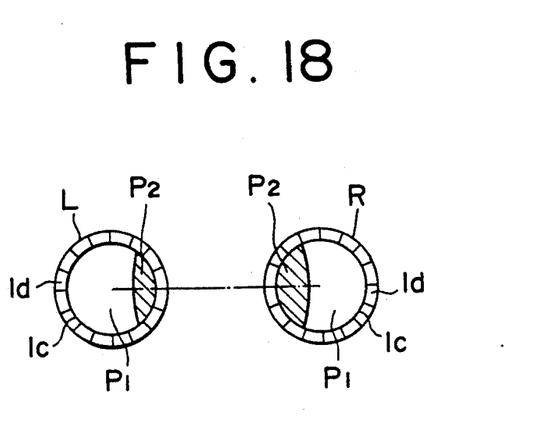
FIGS. 18 and 20 are explanatory views showing the bright and dark portions of the left view field and the bright and dark portions of the left view field.

By the way, in the stereomicroscope shown in FIG. 9, since the optical path 5a of the illuminating optical system 5 is different from the optical paths 3s and 4s of the first and the second observing optical systems 3 and 4 on the objective lens 2, the pupil area 1c does not come to have a uniform brightness when the eye 1 is looked from the oculars 8a and 8b of the observing optical systems 3 and 4. That is, as is shown in FIG. 18, a left-hand side area P1 of the pupil area 1c becomes bright in a left view field L and the right-hand side area P2 becomes dark owing to inversion. In the right view field R, as is shown in FIG. 18, the right-hand side area P1 of the pupil area 1c becomes bright and the left-hand side area P2 becomes dark owing to inversion.

In this way, the position of the area P1 which becomes bright and the position of the area P2 which becomes dark in the pupil area 1c are different depending on the left view field L and the right view field R. Because of the foregoing, there arises such a problem as that image fusion of the pair of eyes becomes difficult to obtain and a surgical operation becomes very difficult to perform.

Figure 19:
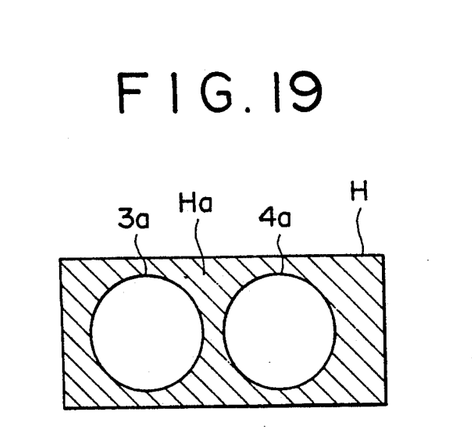
FIG. 19 is an explanatory view showing the illuminated area on the half mirror.
Figure 20:
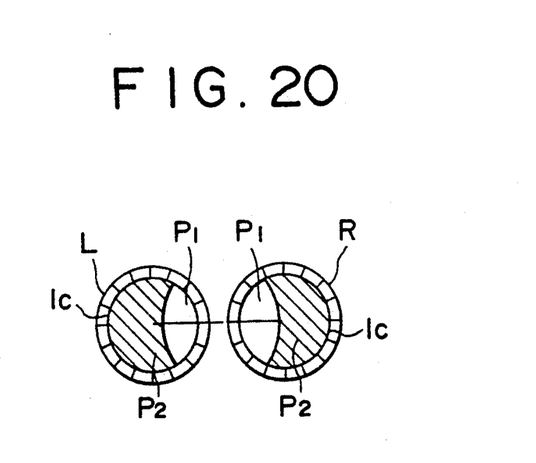

Also, there is another example of the prior art in which a half mirror H is installed as indicated by the broken line of FIG. 9 and the eye 1 is illuminated from an outside position Ha of the first and second observing optical paths 3a and 4a as shown in FIG. 19. However, this prior art does not provide a uniform brightness at the pupil area as in the above-mentioned example. That is, the area P1 which becomes bright and the area P2 which becomes dark in the pupil area 1c are different depending on the left view field L and the right view field R as shown in FIG. 20. Therefore, an image fusion of the pair of eyes becomes difficult to obtain and a surgical operation becomes difficult to performed.

SUMMARY OF THE INVENTION

The object of the present invention is to provide a stereomicroscope in which the pupil area has a uniform brightness so that it can be observed through the left and right view fields.

The feature of the present invention is that it further includes first and second illuminating optical systems for illuminating an eye to be tested about the optical axes of first and second observing optical systems.

3

DETAILED DESCRIPTION OF THE EMBODIMENTS

The embodiments of the present invention will now be described with reference to the drawings.

Figure 1:
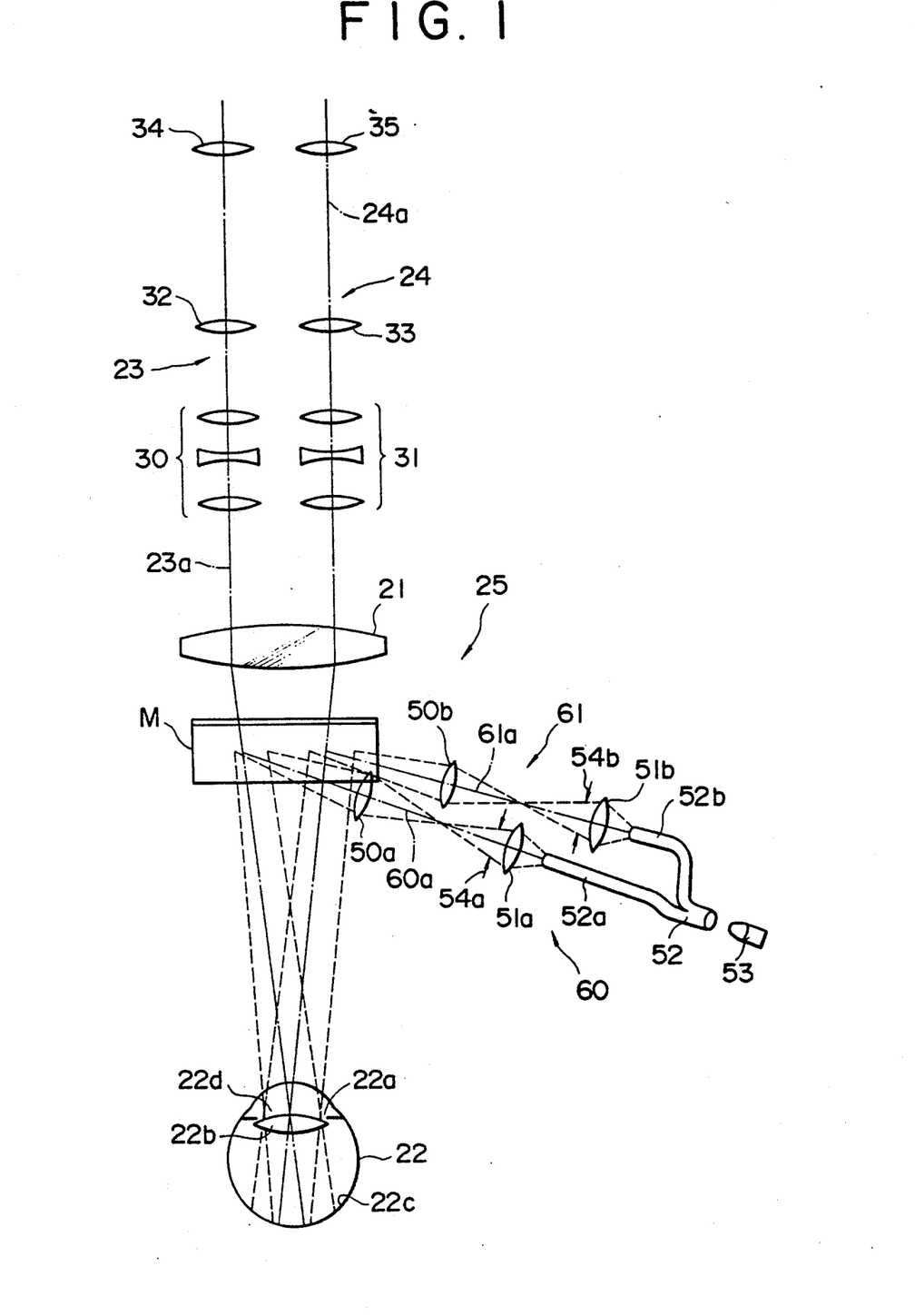
FIG. 1 is a view schematically showing the arrangement of an optical system of a stereomicroscope according to the present invention.
Figure 2:
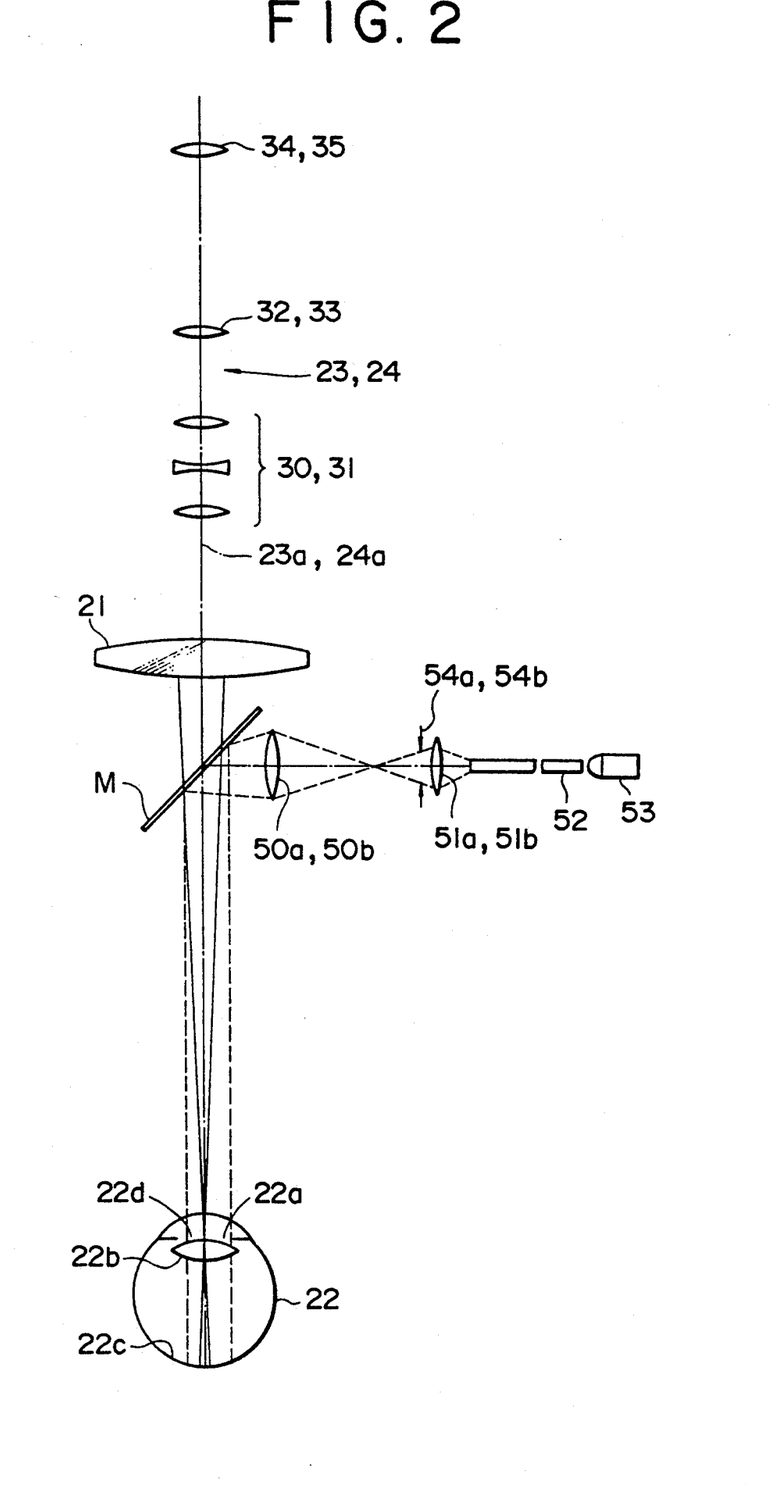
FIG. 2 is a side view showing the arrangement of the optical system of the stereomicroscope.

FIGS. 1 and 2 are diagrams schematically showing the arrangement of the optical system of the stereomicroscope used for a surgical operation for, for example, cataract and the like. This stereomicroscope includes an objective lens 21 facing with an eye 22 to be tested, first and second observing optical systems 23 and 24 for three-dimensionally observing the eye 22, and an illuminating system 25 for illuminating the eye 22.

The first and second observing optical systems 23 and 24 comprise observing zoom lenses 30 and 31, imaging lenses 32 and 33, and oculars 34 and 35.

The illuminating system 25 comprises a half mirror M, projecting lenses 50a and 50b, diaphragms 54a and 54b, condenser lenses 51a and 51b, a light guide 52, and an illuminating lamp 53. The light guide 52 has guide tubes 52a and 52b for guiding light emitted from the illuminating lamp 53 toward the condenser lenses 51a and 51b, the intensity of light emitted from the guide tubes 52a and 52b is set to be even. The diaphragms 54a and 54b are in conjugate relation with the pupil 22a of the eye 22.

And the half mirror M, the projecting lens 50a, the diaphragm 54a, the condenser lens 51a, the light guide tube 52a, and the illuminating lamp 53 constitute a first illuminating optical system 60. Similarly, the half mirror M, the projecting lens 50b, the diaphragm 54b, the condenser lens 51b, the light guide tube 52b, and the illuminating lamp 53 constitute a second illuminating optical system 61. The optical axes 60a and 61a of the first and second illuminating optical systems 60 and 61 are common with the optical axes 23a and 24a of the first and second observing optical systems between the half mirror M and the eye 22.

4

When light is emitted from the illuminating lamp 53, a part of the light is emitted toward the condenser lens 51a passing through the guide tube 52a of the light guide 52. Such emitted light illuminates the eye 22 through the condenser lens 51a, the diaphragm 54a, the projecting lens 50a, and the half mirror M.

On the other hand, a different part of the light emitted from the illuminating lamp 53 is emitted toward the condenser lens 51b passing through the guide tube 52b of the light guide 52. Such emitted light illuminates the eye 22 through the condenser lens 51b, the diaphragm 54b, the projecting lens 50b and the half mirror M.

Illuminating light illuminated the eye 22 reaches the eye fundus 22c through the crystal body 22b of the eye 22 and illuminates the eye fundus 22c. Reflected light by the eye fundus 22c reaches the observing optical systems 23 and 24 through the crystal body 22b, the half mirror M and the objective lens 21.

Figure 3:
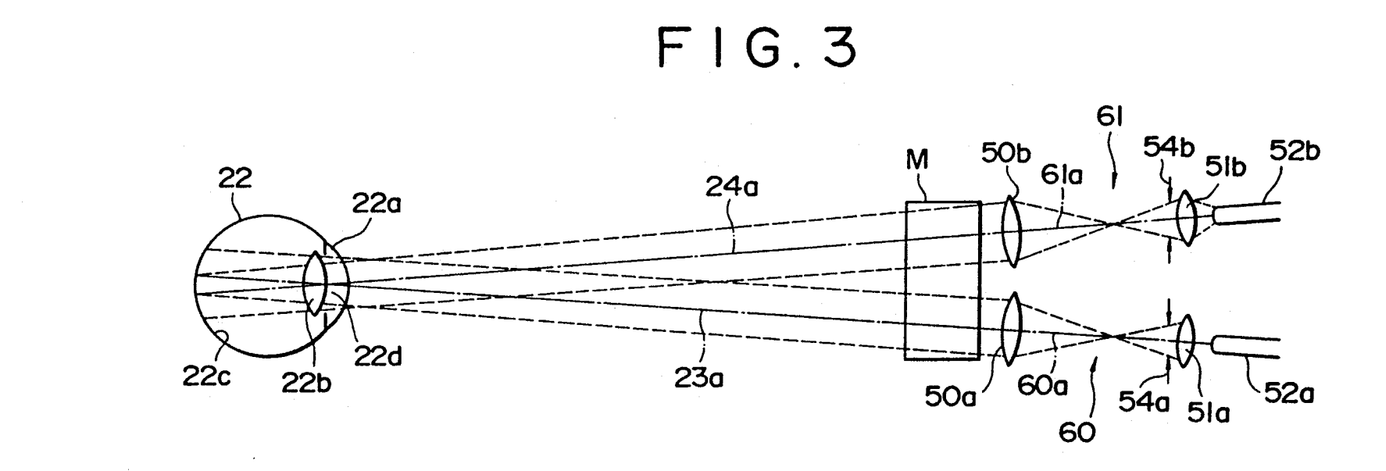
FIG. 3 is an explanatory view showing the arrangement of first and second illuminating optical systems.

By the way, one part of the optical axes 60a and 61a of the first and second illuminating optical systems 60 and 61, as shown in FIG. 3, are common with the optical axes 23a and 24a of the first and second observing optical systems between the half mirror M and the eye 22. Owing to the foregoing arrangement, the eye fundus 22c is illuminated around the optical axes 23a and 24a of the first and second observing optical systems.

Therefore, most part of the reflected light of the illuminating light reaches the observing optical systems 23 and 24 through the crystal body 22b, the half mirror M and the objective lens 21, and the pupil area 22d comes to have a uniform brightness when looked from the observing optical systems 23 and 24.

Figure 4A:
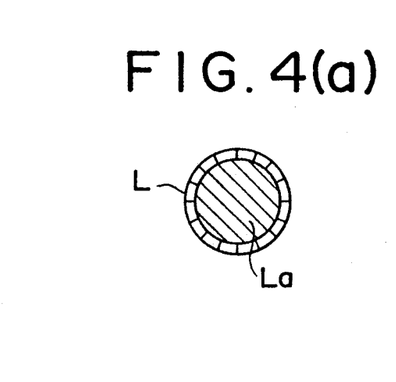
FIG. 4a and 4b is an explanatory view of the left and right view fields of an observing optical system.
Figure 4B:
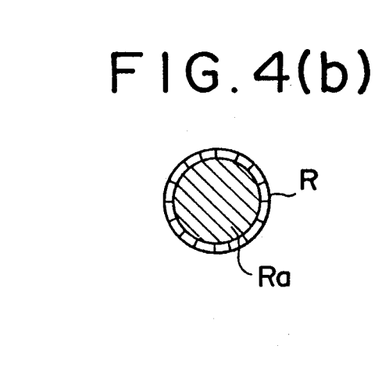

That is, as is shown in FIGS. 4(a) and 4(b), the pupil area La of the left view field L comes to have a uniform brightness when looked through the ocular 34 of the observing optical system 23. Likewise, the pupil area Ra of the right view field R also comes to have a uniform brightness when looked through the ocular 35. Therefore, an image fusion of each eye of the left and right view fields L and R becomes easy, a turbid portion of the crystal body can be found with ease, and a surgical operation of a sclera becomes easy to perform.

Also, as the stereomicroscope uses a single half mirror M, no displacement of the left and right optical axes occurs (this is essential to a stereoscopic observation) and optical adjustment becomes easy to perform. Therefore, there can be provided a stereomicroscope which is inexpensive and excellent in performance. In FIG. 4, the reference characters Lb and Rb denote irises.

Figures 5, 6:
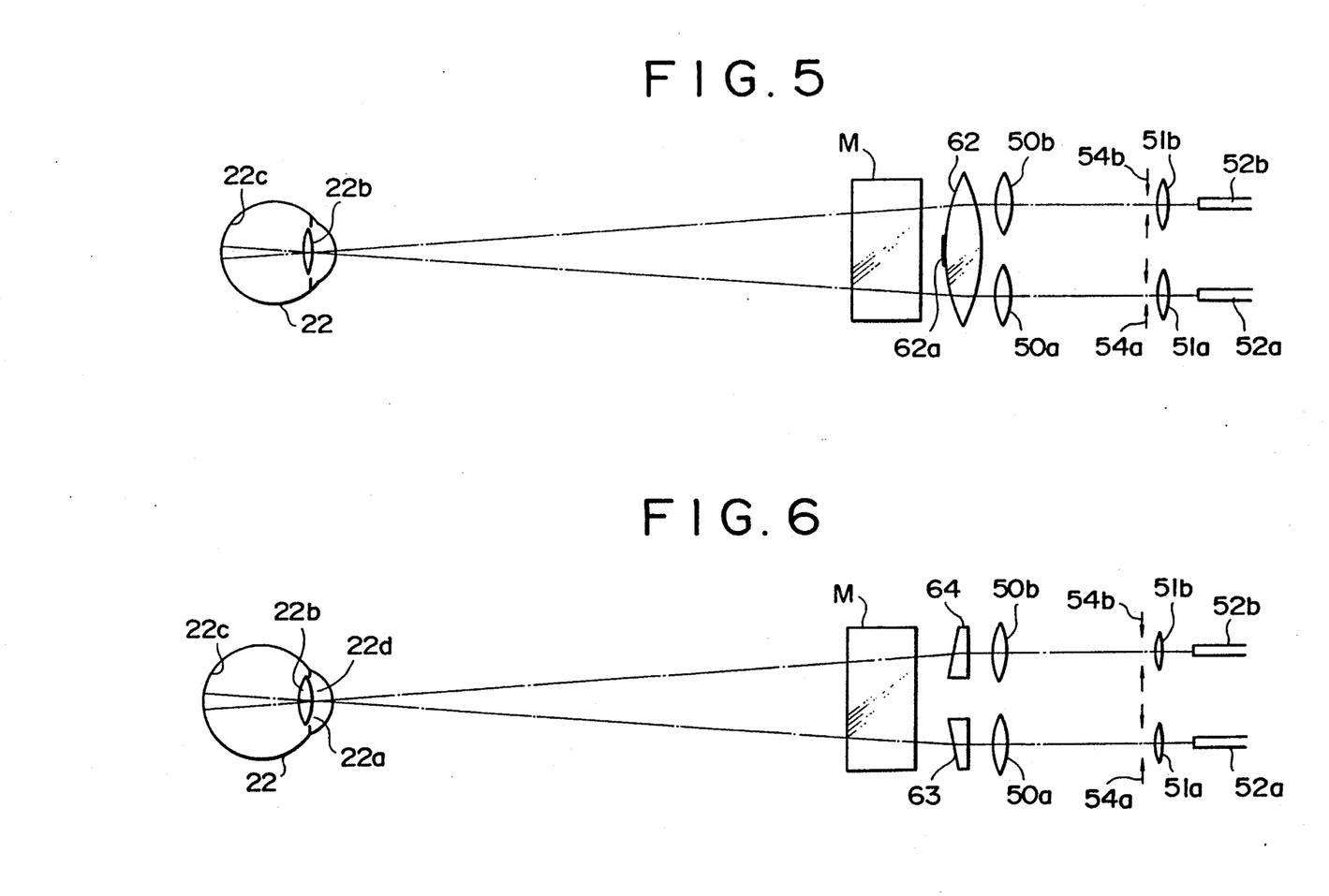
FIG. 5 is an explanatory view of a second embodiment.
FIG. 6 is an explanatory view of a third embodiment.

FIG. 5 shows the second embodiment, in which a deflecting lens (deflecting element) 62 for displacing the optical axes 60 and 61 of the first and second illuminating optical systems 60 and 61 is disposed between the projecting lenses 50a, 50b and the half mirror M. And the optical axes between the projecting lenses 50a, 50b and the condenser lenses 51a, 51b are arranged in parallel relation. Owing to the foregoing arrangement, the optical axes 23a and 24a of the first and second observing optical systems 23 and 24 and the optical axes 60a and 61b of the first and second optical systems 60 and 61 can be made common with ease. The symbolic numeral 62a denotes a shaded central portion of the deflecting lens 62.

FIG. 6 shows the third embodiment using prisms 63 and 64 instead of the deflecting lens 62 of FIG. 5.

Figure 7:
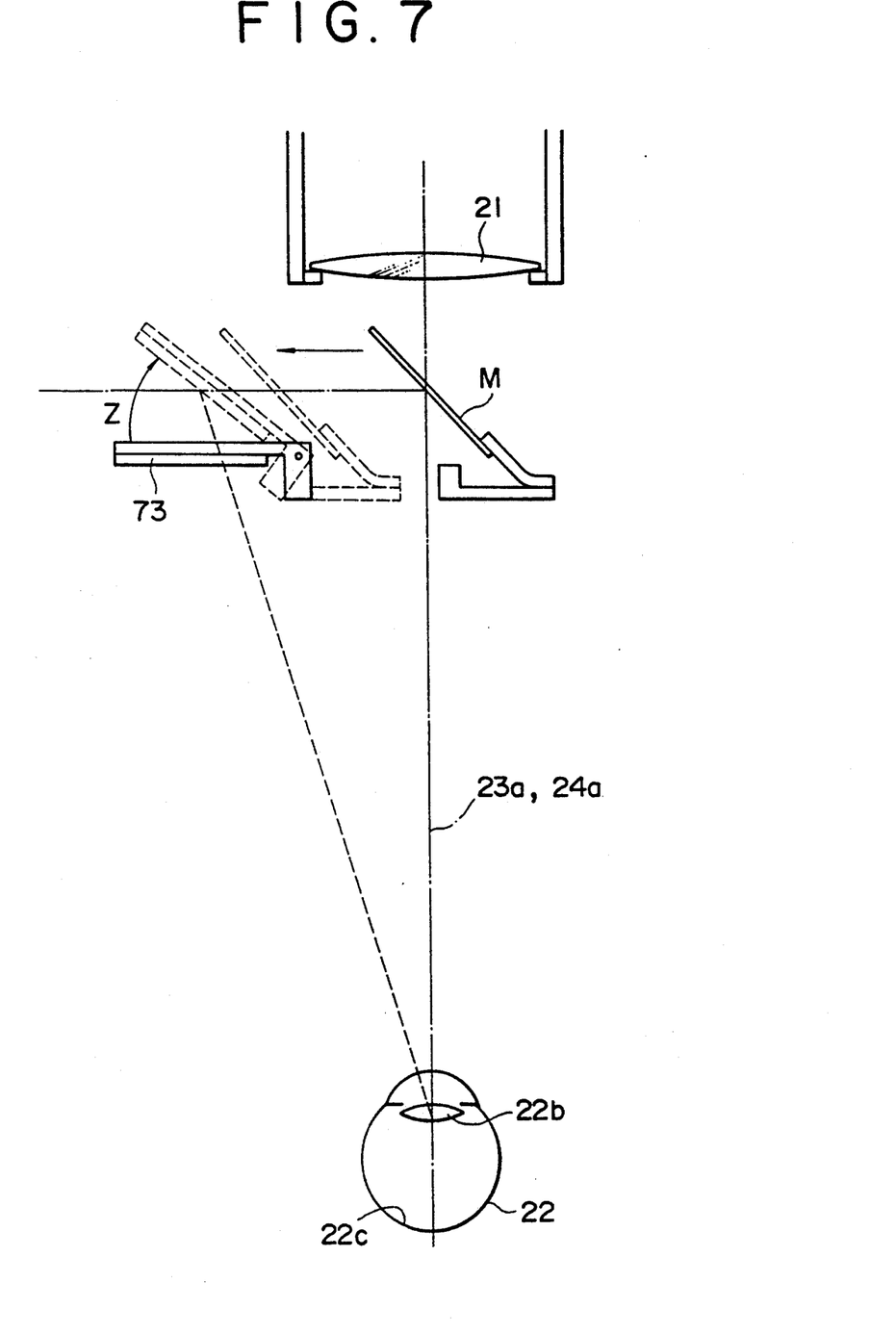
FIG. 7 is an explanatory view of a fourth embodiment.

FIG. 7 shows the fourth embodiment, in which the half mirror M can be moved to a position indicated with a broken line, so that the eye 22 can be illuminated in a different angle from that of the first and second optical systems.

Figure 8:
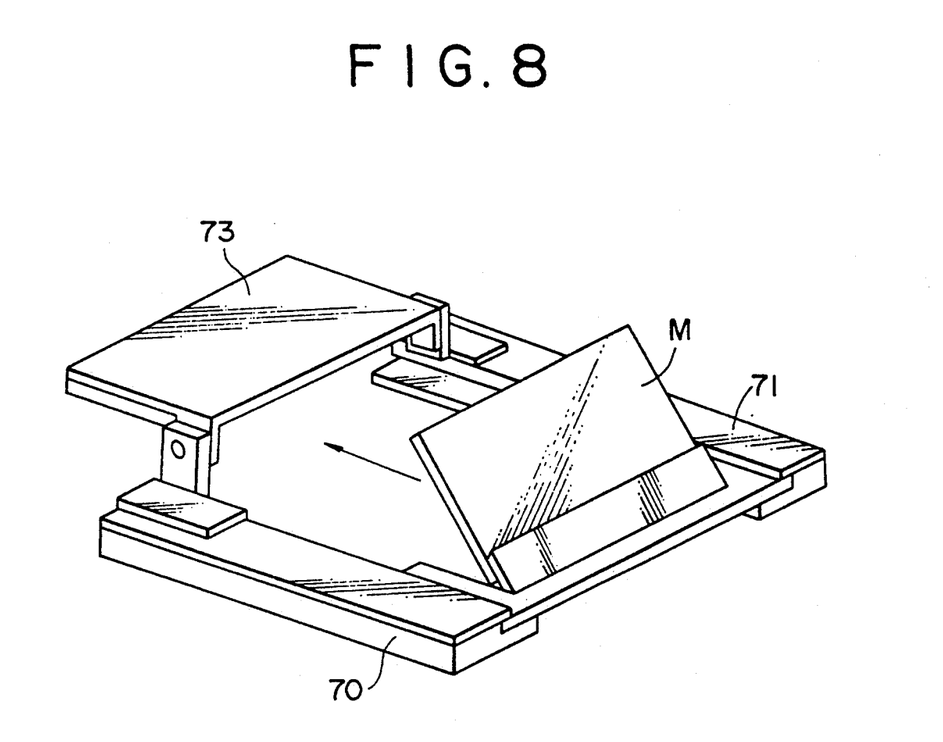
FIG. 8 is an explanatory view of a moving mechanism of a half mirror.

The half mirror M, as shown in FIGS. 7 and 8, can be moved in the direction as indicated by an arrow along a pair of guide rails 70 and 71. At the end of the guide rails 70 and 71, a reflecting mirror 73 is disposed in such a manner as to be able to turn in the direction as indicated by an arrow Z.

Accordingly, when the half mirror M is moved to the position indicated by the broken line of FIG. 7 and the reflecting mirror 73 is turned to the position as indicated by the broken line, illuminating light is reflected by the reflecting mirror 73 to illuminate the eye 22 in a different angle from that of the optical axes 23a and 24a of the first and second observing optical systems 23 and 24, and the eye 22 can directly be observed without a using half mirror.

What is claimed is:

1. A stereomicroscope including an objective lens facing an eye, and first and the second observing optical systems for three-dimensionally observing the eye through said objective lens, said stereomicroscope further including:

a light splitting element movable between inside and outside positions of the optical paths of said first and second observing optical systems;

first and the second illuminating optical systems for illuminating said eye around the optical axes of said first and second observing optical systems through said splitting element when said splitting element is moved into said optical paths; and a reflecting mirror movable between inside and outside positions of said optical paths of said first and second illuminating optical systems, the illuminating light of said first and second illuminating optical systems illuminating said eye in a different angle from that of the optical axes of said first and second observing optical paths through said reflecting mirror when said reflecting mirror is moved into said optical paths.

2. A stereomicroscope according to claim 1, wherein said first and second illuminating optical systems have a deflecting element for arranging the optical axes of said first and second illuminating optical systems in parallel relation.

3. A stereomicroscope according to claim 2, wherein said deflecting element comprises a deflecting lens for displacing the optical axes.

4. A stereomicroscope according to claim 2, wherein said deflecting element comprises a prism.

* * * * *